(12) United States Patent
Madan et al.

(10) Patent No.: US 11,058,902 B2
(45) Date of Patent: Jul. 13, 2021

(54) COMPOSITIONS AND METHODS FOR TREATING DISEASE ASSOCIATED WITH PERMEABILITY OF INTESTINAL EPITHELIUM

(71) Applicants: 9 Meters Biopharma, Inc., Raleigh, NC (US); NORTH CAROLINA STATE UNIVERSITY, Raleigh, NC (US)

(72) Inventors: Jay P. Madan, Raleigh, NC (US); Anthony Blikslager, Raleigh, NC (US); Sandeep Laumas, Raleigh, NC (US)

(73) Assignees: 9 METERS BIOPHARMA, INC., Raleigh, NC (US); NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 16/484,497

(22) PCT Filed: Feb. 12, 2018

(86) PCT No.: PCT/US2018/017813
§ 371 (c)(1),
(2) Date: Aug. 8, 2019

(87) PCT Pub. No.: WO2018/148655
PCT Pub. Date: Aug. 16, 2018

(65) Prior Publication Data
US 2019/0358289 A1 Nov. 28, 2019

Related U.S. Application Data

(60) Provisional application No. 62/457,279, filed on Feb. 10, 2017.

(51) Int. Cl.
| A61K 38/00 | (2006.01) |
| A61P 1/04 | (2006.01) |
| A61K 38/08 | (2019.01) |
| A61K 45/06 | (2006.01) |
| A61K 35/741 | (2015.01) |

(52) U.S. Cl.
CPC .............. *A61P 1/04* (2018.01); *A61K 35/741* (2013.01); *A61K 38/08* (2013.01); *A61K 45/06* (2013.01)

(58) Field of Classification Search
CPC .. A61K 38/08; A61K 2300/00; A61K 35/741; A61K 45/06; A61P 1/00; A61P 9/10; A61P 1/04; A61P 1/16; A61P 31/04; C07C 53/10; C07K 7/06
See application file for complete search history.

(56) References Cited

U.S. PATENT DOCUMENTS

| 5,665,389 A | 9/1997 | Fasano |
| 5,827,534 A | 10/1998 | Fasano |
| 5,945,510 A | 8/1999 | Fasano |
| 6,458,925 B1 | 10/2002 | Fasano |
| 6,670,448 B2 | 12/2003 | Fasano |
| 6,936,689 B2 | 8/2005 | Fasano |
| 7,026,294 B2 | 4/2006 | Fasano et al. |
| 7,189,696 B2 | 3/2007 | Fasano |
| 7,531,504 B2 | 5/2009 | Fasano |
| 7,531,512 B2 | 5/2009 | Fasano et al. |
| 7,582,603 B2 | 9/2009 | Fasano |
| 8,034,776 B2 | 10/2011 | Fasano et al. |
| 8,168,594 B2 | 5/2012 | Paterson et al. |
| 8,183,211 B2 | 5/2012 | Fasano |
| 8,198,233 B2 | 6/2012 | Tamiz et al. |
| 8,299,017 B2 | 10/2012 | Paterson et al. |
| 8,557,763 B2 | 10/2013 | Tamiz et al. |
| 8,785,374 B2 | 7/2014 | Tamiz |
| 8,796,203 B2 | 8/2014 | Paterson et al. |
| 8,957,032 B2 | 2/2015 | Alkan et al. |
| 9,051,349 B2 | 6/2015 | Callens et al. |
| 9,241,969 B2 | 1/2016 | Paterson et al. |
| 9,265,811 B2 | 2/2016 | Paterson et al. |
| 9,279,807 B2 | 3/2016 | Fasano et al. |
| 2011/0275562 A1 | 11/2011 | Alkan et al. |
| 2013/0244935 A1* | 9/2013 | Besner ................. A61K 38/177 514/9.6 |
| 2015/0164978 A1 | 6/2015 | Paterson et al. |
| 2016/0022760 A1* | 1/2016 | Perrow ..................... A61P 3/00 514/21.7 |
| 2016/0349257 A1 | 12/2016 | Bai et al. |
| 2016/0355551 A1 | 12/2016 | Paterson et al. |

(Continued)

FOREIGN PATENT DOCUMENTS

| WO | WO-0007609 A1 * | 2/2000 | ............... C07K 7/08 |
| WO | WO-2009137572 A2 * | 11/2009 | .......... C07K 5/0806 |
| WO | 2016011335 A1 | 1/2016 | |

OTHER PUBLICATIONS

Elaine Luo "Ischemic colitis" in Healthline. Accessed Sep. 2020 at <https://www.healthline.com/health/ischemic-colitis> 2018 (Year: 2018).*
Khaleghi et al. The potential utility of tight junction regulation in celiac disease: focus on larazotide acetate. 2015. Therap Adv Gastroenterol. Jan. 2016; 9(1): 37-49 (Year: 2015).*
Monkmuller et al. Endoscopic Spectrum of Ischemic Colitis. 2013. Video Journal and Encyclopedia of GI Endoscopy vol. 1, Issue 2, Oct. 2013, pp. 346-347 (Year: 2013).*

(Continued)

*Primary Examiner* — James H Alstrum-Acevedo
*Assistant Examiner* — Mercy H Sabila
(74) *Attorney, Agent, or Firm* — Morgan, Lewis & Bockius LLP

(57) ABSTRACT

The present invention provides methods for treating disorders associated with intestinal barrier dysfunction and increased intestinal permeability. The invention involves administering an effective amount larazotide or a larazotide derivative to a subject or a patient in need thereof.

24 Claims, 8 Drawing Sheets

Specification includes a Sequence Listing.

(56) References Cited

U.S. PATENT DOCUMENTS

2018/0133281 A1     5/2018   Tamiz
2018/0271932 A1     9/2018   Perrow et al.

OTHER PUBLICATIONS

Molitoris et al. Ischemia-induced Loss of Epithelial Polarity. J Clin Invest. Oct. 1989 84(4): 1334-1339 (Year: 1989).*
Petri et al., "Environmental enteropathy and malnutrition: do we know enough to intervene?", BMC Medicine 2014, vol. 12, No. 187, pp. 1-5.
Gopalakrishnan, et al., "Larazotide acetate promotes tight junction assembly in epithelial cells", Peptides 35 (2012) pp. 95-101.
Gopalakrishnan, et al., "Larazotide acetate regulates epithelial tight junctions in vitro and in vivo", Peptides 35 (2012) pp. 86-94.
International Search Report and Written Opinion for International Application No. PCT/US2018/017813, dated May 2, 2018, 13 pages.
Khaleghi, et al., "The Potential Utility of Tight Junction Regulation in Celiac Disease: Focus on Larazotide Acetate", Therapeutic Advances in Gastroenterology, 2016, vol. 9, No. 1, pp. 37-49.
Monkemuller, et al., "Endoscopic Spectrum of Ischemic Colitis: Video Journal and Encyclopedia of GI Endoscopy", 2013, vol. 1, No. 2, pp. 1-6.
Tan et al., "Berberine Ameliorates Intestinal Mucosal Barrier Damage Induced by Peritoneal Air Exposure," Biol. Pharm. Bull., 2015, vol. 38, No. 1, pp. 122-126.

* cited by examiner

Negative control
No 1° Ab:DAPI

1 µM Larazotide
Time 240'

10 µM Larazotide
Time 240'

COMPOSITIONS AND METHODS FOR TREATING DISEASE ASSOCIATED WITH PERMEABILITY OF INTESTINAL EPITHELIUM

PRIORITY

This application claims priority to, and the benefit of, U.S. Provisional Application No. 62/457,279.

FIELD OF THE INVENTION

The present invention provides compositions and methods for treating diseases and disorders associated with intestinal barrier dysfunction.

BACKGROUND

The intestinal epithelium is the layer of cells that forms the luminal surface of the small and large intestines of the gastrointestinal (GI) tract, and represents the largest interface (more than 400 m$^2$) between the external environment and the internal milieu.

The intestinal epithelium has two important functions: absorbing nutrients and providing a barrier against harmful environmental substances such as bacteria, viruses, toxins, and food allergens.

The barrier properties of the intestinal epithelium are regulated by specialized plasma membrane structures known as tight junctions. Alterations in tight junctions can result in disruptions of the intestinal barrier functions and increased intestinal permeability. An intact intestinal barrier prevents the permeation of pathogens, antigens, endotoxins, and other proinflammatory substances into the body, whereas intestinal disintegrity allows their entry, which may trigger local or systemic inflammation and disease.

Accordingly, there is a need for effective treatments for intestinal barrier dysfunction for treating, ameliorating, and slowing progression of disease.

SUMMARY OF THE INVENTION

The present invention provides methods for treating disorders associated with intestinal barrier dysfunction and increased intestinal permeability. The invention involves administering an effective amount larazotide or a larazotide derivative to a subject or a patient in need thereof, to repair damaged intestinal epithelium and/or reduce intestinal leakiness that can trigger or exacerbate disease.

Intestinal barrier dysfunction and increased intestinal permeability can be linked to various diseases ranging from intestinal disorders such as enterocolitis (e.g., necrotizing enterocolitis), ischemic colitis, as well as sepsis and liver disease including nonalcoholic fatty liver disease (NAFLD), nonalcoholic steatohepatitis (NASH), and cirrhosis (e.g., alcohol cirrhosis).

In various embodiments, an effective amount of larazotide or larazotide derivative is administered to a subject having or at risk of necrotizing enterocolitis or ischemic colitis. Upon treatment with larazotide or larazotide derivative, improvement of intestinal barrier function can be obtained with amelioration of disease symptoms.

In various embodiments, the present invention provides for the treatment of liver disease. For example, in some embodiments, the subject may have a fatty liver disease including, but not limited to non-alcoholic fatty acid liver disease (NAFLD), non-alcoholic steatohepatitis (NASH). In some embodiments, improvements in intestinal barrier function limit the amount of toxins such as LPS that enter circulation and which can ultimately exacerbate disease or promote disease progression.

In various embodiments, the invention involves pharmaceutical compositions comprising larazotide or derivatives thereof, including sustained release or controlled release formulations that avoid accumulation of inactive fragments that may act as competitive inhibitors. For example, the sustained release formulation may deliver and/or functionally release from about 0.5 to about 5 mg of larazotide over the course of at least about 2 hours. In some embodiments, the composition releases at least 1 mg of larazotide over the course of at least about 3 hours, as can be determined for example, using simulated intestinal fluid.

In various embodiments, the present invention provides pharmaceutical compositions comprising larazotide or derivatives thereof in various formulations for oral delivery to the GI, including tablets, pills, pellets, and capsules, and including capsules containing peptide-coated particles, liquids, emulsions, or gels. In some embodiments, the composition comprises capsules containing delayed release particles, gels, or other biodegradable matrix.

In some embodiments, the patient may receive adjunct therapy, which in some embodiments is synergistic with larazotide treatment. In some embodiments, the additional therapeutic agent is an antibacterial agent such as an antibiotic, an antiviral agent, and/or a probiotic, which can ameliorate associated dysbiosis in a synergistic manner with larazotide treatment.

Other aspects and embodiments of the invention will be apparent from the following detailed description.

DETAILED DESCRIPTION

Figure 1:
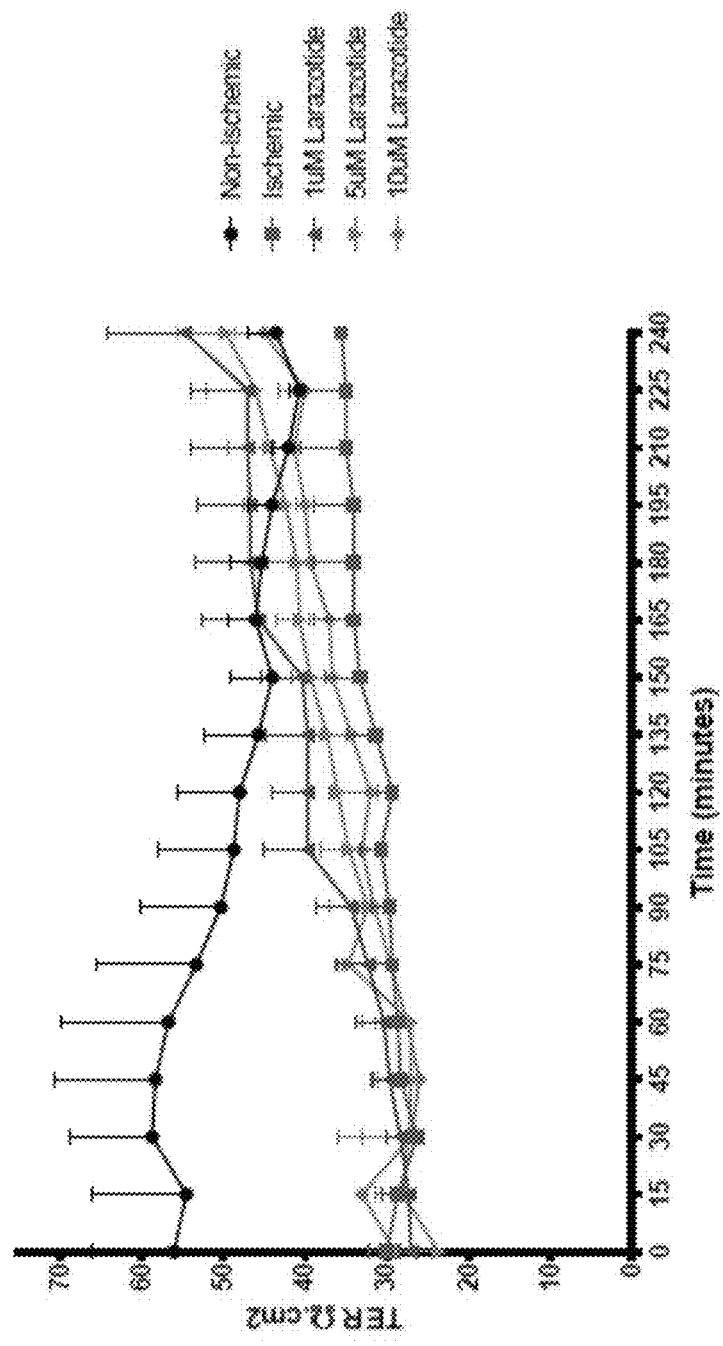
FIG. 1 shows that ischemic-injured tissues treated with larazotide alone showed a dose-dependent and significant (P<0.05) increase in recovery of TER as compared to untreated ischemic tissues.

The present invention provides methods for treating disorders associated with intestinal barrier dysfunction and increased intestinal permeability. The invention involves administering an effective amount larazotide or a larazotide derivative to a subject or a patient in need thereof.

Intestinal barrier dysfunction and increased intestinal permeability can be linked to various diseases ranging from intestinal disorders such as enterocolitis (e.g., necrotizing enterocolitis), ischemic colitis, as well as sepsis and liver disease, including nonalcoholic fatty liver disease (NAFLD), nonalcoholic steatohepatitis (NASH), and cirrhosis (e.g., alcohol cirrhosis).

In some embodiments, the present invention provides for treatment of necrotizing enterocolitis (NEC). Necrotizing enterocolitis is a medical condition primarily seen in premature infants, and is characterized by variable damages to the intestinal lining, ranging from mucosal injury to full-thickness necrosis and perforation. The presence and severity of necrotizing enterocolitis is graded using the staging system of Bell et al., *J. Ped. Surg.*, 15:569 (1980):

| | |
|---|---|
| Stage I (Suspected NEC) | Systemic manifestations—temperature instability, lethargy, apnea, bradycardia Gastrointestinal manifestations poor feeding, increased pregavage residuals, emesis (may be bilious or test positive for occult blood), mild abdominal distention, occult blood in stool (no fissure) Non-specific or normal radiological signs |
| Stage II (Definite NEC) | Above signs and symptoms plus persistent occult or gross gastrointestinal bleeding, marked abdominal distention Abdominal radiographs showing significant intestinal distention with ileus, small-bowel separation (edema in bowel wall or peritoneal fluid), unchanging or persistent "rigid" bowel loops, pneumatosis intestinalis, portal venous gas |
| (NEC) | Laboratory changes (thrombocytopenia, metabolic acidosis) |
| Stage III (Advanced NEC) | Above signs and symptoms plus deterioration of vital signs, evidence of septic shock, or marked gastrointestinal hemorrhage, hypotension, striking abdominal distension, peritonitis Abdominal radiographs showing pneumoperitoneum in addition to findings listed for Stage II Additional laboratory changes (metabolic and respiratory acidosis, disseminated intravascular coagulation) |

In various embodiments, an effective amount of larazotide or larazotide derivative is administered to a subject having stage 1 NEC (suspected NEC), or stage II NEC, or stage II NEC, or advanced NEC. Upon treatment with an effective amount of larazotide or larazotide derivative, improvement of intestinal barrier function can be obtained, with ameliorating of disease symptoms.

In some embodiments, the invention provides compositions and methods for treating an ischemic intestinal disorder, including associated shock, sepsis, clot formation in the gut, and intestinal volvulus. Ischemic colitis is a medical condition in which inflammation and injury of the large intestine result from inadequate blood supply. Ischemic colitis occurs with greater frequency in the elderly. Causes of the reduced blood flow can include changes in the systemic circulation (e.g. low blood pressure) or local factors such as constriction of blood vessels or a blood clot. In some embodiments, the subject has mild to moderate ischemic colitis, or in other embodiments, severe ischemic colitis.

In various embodiments, the present invention provides for the treatment of a liver disease. For example, in some embodiments, the subject has a fatty liver disease including, but not limited to non-alcoholic fatty acid liver disease (NAFLD), non-alcoholic steatohepatitis (NASH), or a fatty liver disease resulting from hepatitis, obesity, diabetes, insulin resistance, hypertriglyceridemia, abetalipoproteinemia, glycogen storage disease, Weber-Christian disease, Wolmans disease, acute fatty liver of pregnancy, and lipodystrophy. In some embodiments, improvements in intestinal barrier function limit the amount of toxins such as LPS that enter circulation and which can ultimately exacerbate disease or promote disease progression. In some embodiments, the subject has NASH.

In an embodiment, the present invention provides for the treatment of a patient with NAFLD. NAFLD represents a spectrum of disease occurring in the absence of alcohol abuse. It is characterized by the presence of steatosis (fat in the liver) and may represent a hepatic manifestation of the metabolic syndrome (including obesity, diabetes and hypertriglyceridemia). The severity of NAFLD ranges from the relatively benign isolated predominantly macrovesicular steatosis (i.e., nonalcoholic fatty liver or NAFL) to nonalcoholic steatohepatitis (NASH). NASH is characterized by the histologic presence of steatosis, cytological ballooning, scattered inflammation and pericellular fibrosis. Hepatic fibrosis resulting from NASH may progress to cirrhosis of the liver or liver failure, and in some instances may lead to hepatocellular carcinoma. In some embodiments, methods of the invention reduce, ameliorate, or eliminate one or more symptoms of NAFLD or NASH, including any of the symptoms described herein (e.g., liver cirrhosis or liver fibrosis). In some embodiments, method of the invention prevents or slows the progression of NAFLD or NASH to hepatocellular carcinoma.

In some embodiments, the present invention provides for the treatment of a patient with hepatitis. In exemplary embodiments, the hepatitis may be caused by viruses, alcohol, drugs, and the like. In an embodiment, the present invention provides for the treatment of a patient with hepatitis A, hepatitis B, hepatitis C, hepatitis D, or hepatitis E. In another embodiment, the present invention provides for the treatment of alcoholic hepatitis. In a further embodiment, the present invention provides for the treatment of autoimmune hepatitis. Symptoms of hepatitis include fatigue, flu-like symptoms, dark urine, pale stool, abdominal pain, loss of appetite, unexplained weight loss, and jaundice. Chronic hepatitis is also associated with cirrhosis and hepatocellular carcinoma. In various embodiments, methods of the invention reduce, ameliorate, or eliminate one or more symptoms of hepatitis, including any of the symptoms described herein.

In some embodiments, the subject has or is at risk of sepsis. Sepsis is a life-threatening condition that arises when the body's response to infection causes injury to its own tissues and organs. Improvements in intestinal barrier function limit the amount of bacteria and toxins such as LPS that enter circulation and which can ultimately exacerbate disease.

In various embodiments, methods of the invention are useful in treating a mammalian subject, including a human subject. In some embodiments, methods of the invention relate to treatment of a pediatric human subject (including for the prevention or treatment of necrotizing enterocolitis). In various embodiments, the pediatric human subject may be about 1 week old to about 12 years of age. In some embodiments, the pediatric subject is an infant, such as a premature infant, which may be afflicted with necrotizing enterocolitis. In some embodiments, the premature infant is born at less than 37 weeks of gestational age. In other embodiments, the pediatric subject is a full term infant, for example, an infant who is born later than about 37 weeks of gestational age. In some embodiments, the pediatric subject may exhibit one or more of prenatal asphyxia, shock, sepsis, or congenital heart disease. In various embodiments, the pediatric subject is of low birth weight.

In other embodiments, methods of the invention relate to treatment of an adult human subject including a geriatric human subject, including for treatment of an ischemic intestinal condition (e.g., ischemic colitis), sepsis, or liver disease.

In various embodiments, the methods of the invention comprise treating a subject with larazotide or derivative thereof. Larazotide is a peptide agent that promotes tight junction integrity in the gastrointestinal tract (GI). Larazotide has the amino acid sequence: Gly Gly Val Leu Val Gln Pro Gly (SEQ ID NO:1), and can be formulated for systemic or targeted release in affected portions of the GI (e.g., small intestine and/or large intestine). Larazotide has been shown in clinical trials to exhibit benefit at reducing celiac disease symptoms, particularly at lower doses (e.g., 0.5 mg dose). See US 2016/0022760, which is hereby incorporated by reference in its entirety. Higher doses (e.g., 1 mg and 2 mg doses) showed an attenuation of activity, or no activity at all. In accordance with this disclosure, it is believed that an aminopeptidase located within the brush borders of the lumen surface may create larazotide-derived fragments, including fragments missing N-terminal glycine residues. For example, the fragments GVLVQPG (SEQ ID NO:2) and VLVQPG (SEQ ID NO:3) are inactive as tight junction regulators. Moreover, when these two fragments are mixed with full length larazotide, activity is completely abolished. Local buildup of these inactive larazotide fragments (due to excessive larazotide) may in fact compete and block function of the peptide. This would explain clinical observations that low doses of larazotide work best by avoiding the reservoir of competing inactive fragments. Thus, in some embodiments, controlled release or sustained release formulations are employed to increase effectiveness of larazotide or derivative.

In some embodiments, the active agent is a larazotide derivative, for example, having one or more amino acid modifications, such as amino acid substitutions, deletions, and/or insertions. For example, the derivative may have 1, 2, 3, or 4 amino acid modifications independently selected from amino acid deletions, insertions, and/or substitutions with respect to SEQ ID NO:1. Exemplary larazotide derivatives are described in U.S. Pat. Nos. 8,785,374, 8,957,032, and 9,279,807, which are hereby incorporated by reference in their entirety. In some embodiments, the derivative has one or more non-genetically encoded amino acids, or one or more (or all) D-amino acids. The term "larazotide" or "larazotide treatment" refers to treatment with larazotide or a derivative that promotes tight junction integrity.

Larazotide or derivative may be administered in any suitable form, including as a salt. For example, larazotide or derivative may be administered as an acetate salt. Salts of larazotide, including the acetate salt and hydrochloride salt, are described in US 2013/0281384, which is hereby incorporated by reference in its entirety. Alternative salts may be employed, including any pharmaceutically acceptable salt of the peptide such as those listed in Journal of Pharmaceutical Science, 66, 2-19 (1977) and The Handbook of Pharmaceutical Salts; Properties, Selection, and Use. P. H. Stahl and C. G. Wermuth (eds.), Verlag, Zurich (Switzerland) 2002, which are hereby incorporated by reference in their entirety.

In various embodiments, the larazotide is administered in a sustained release or controlled release formulation. The sustained release or controlled release formulation avoids accumulation of inactive fragments that may act as competitive inhibitors. For example, the formulation may deliver and/or functionally release from 0.5 to about 5 mg of larazotide or derivative, or from about 0.5 to about 4 mg of larazotide or derivative, or from about 0.5 to about 3 mg of larazotide or derivative, or from about 0.5 to about 2 mg of larazotide or derivative, or from about 0.5 to about 1 mg of larazotide or derivative. In various embodiments, the sustained release or controlled release formulation contains at least 1 mg or at least 2 mg of larazotide or derivative. For example, the formulation may contain from about 1 mg to about 5 mg of larazotide or derivative, or about 1 mg to about 3 mg of larazotide or derivative.

The sustained or controlled release formulation may functionally release peptide over the course of at least about 2 hours, or over the course of at least about 2.5 hours, or over the course of at least about 3 hours, or over the course of at least about 4 hours, or over the course of at least about 5 hours. The term "functional release" refers to the release of larazotide or derivative such that the peptide can interact with cells of the intestinal epithelium to promote tight junction assembly. In various embodiments, larazotide is formulated as a plurality of particles that release larazotide at different times in intestinal fluid, or at different locations in the intestine. In other embodiments, the formulation releases larazotide in a form that provides for a local sustained release at one or more locations, including sustained release from particles, gels, emulsions, or biodegradable matrix. In some embodiments, the sustained or controlled release composition (e.g., comprising peptide-containing particles, gels, emulsions, or biodegradable matrix) begins to release peptide starting within about 5 to about 30 minutes of exposure to simulated intestinal fluid, with release of peptide continuing for at least about 180 minutes, or at least about 210 minutes, or at least about 240 minutes, or at least about 280 minutes of exposure to simulated intestinal fluid. Release profiles can be prepared, for example, using particles with different enteric polymer coats and/or different thicknesses of the polymer coats. Exemplary particles are described herein.

In one embodiment, the composition comprising peptide remains essentially intact, or may be essentially insoluble, in gastric fluid. The stability of a gastric-resistant coating can be pH dependent. Delayed-release coatings that are pH dependent will be substantially stable in acidic environments (pH 5 or less), and substantially unstable in near neutral to alkaline environments (pH greater than 5). For example, a delayed-release coating can be employed that will essentially disintegrate or dissolve in near neutral to alkaline environments such as are found in the small intestine. Examples of simulated gastric fluid and simulated intestinal fluid include, but are not limited to, those disclosed in the 2005 Pharmacopeia 23NF/28USP in Test Solutions and/or other simulated gastric fluids and simulated intestinal fluids known to those of skill in the art, for example, simulated gastric fluid and/or intestinal fluid prepared without enzymes.

Alternatively, the stability of the delayed-release coating can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans.

Various methods may be used to formulate and/or deliver the larazotide or derivative to a location of interest. In some embodiments, the larazotide or derivative is formulated for systemic delivery. In other embodiments, the larazotide is formulated for targeted delivery. For example, the compositions described herein may be formulated for targeted delivery to the gastrointestinal tract including the stomach, small intestine, large intestine and rectum including all subsections thereof. By targeting release of larazotide or derivative in the affected region(s) (e.g. duodenum, jejunum and ileum, colon transversum, colon descendens, colon ascendens, colon sigmoidenum and cecum), tight junction integrity at various portions of the GI can be improved.

In some embodiments, the composition is formulated to release in the small intestine, including one or more of the duodenum, jejunum, and/or the ileum. Alternatively or in addition, the composition is formulated to release in the large intestine, including one or more of the cecum, the ascending colon, the transverse colon, the descending colon, and/or the sigmoid colon. For example, in embodiments related to the treatment of ischemic colitis, the larazotide or derivative may be formulated to include delivery to the large intestines.

In various embodiments, the composition may be formulated to have sustained-release profiles, i.e. slow release of the larazotide in the body (e.g., GI tract) over an extended period of time. In various embodiments, the composition may be formulated to have a delayed-release profile, i.e. not immediately release the Larazotide upon ingestion; rather, postponement of the release until the composition is lower in the gastrointestinal tract; for example, for release in the small intestine (e.g., one or more of duodenum, jejunum, ileum) and/or the large intestine (e.g., one or more of cecum, ascending, transverse, descending or sigmoid portions of the colon, and rectum). In an embodiment, the pharmaceutical composition is formulated to have a delayed-release profile as described in, for example, U.S. Pat. No. 8,168,594, the entire contents of which are hereby incorporated by reference.

For example, the larazotide or derivative may be administered to the duodenum, jejunum, and ileum of the patient, as an oral dosage, delayed-release composition that contains larazotide (or derivative)-coated beads that are stable in gastric fluid and unstable in intestinal fluid so as to substantially release the peptide in the duodenum. The composition may further comprise a second population of beads with a pH-dependent coating to affect release of the peptide in the jejunum of the patient. For example, the second population of beads may release the larazotide or derivative about 30 minutes after the beads releasing peptide in the duodenum. The composition may further comprise a third population of beads with a pH-dependent coating to affect release of the peptide in the ileum of the patient. For example, the third population of beads may release the larazotide or derivative at least about 30 minutes after the beads releasing peptide in the jejunum. The oral dosage composition can be in the form of a capsule or tablet. The pH-dependent coating in some embodiments is a 1:1 co-polymer of methacrylic acid and ethyl acrylate, wherein the thickness of the layer determines the release profile of each bead. The beads may have one or more additional coatings such as a base coat, a separating layer, and an overcoat layer.

In an exemplary oral dosage composition, an effective amount of larazotide (e.g., as the acetate salt) is provided in first delayed-release particles that are capable of releasing larazotide or derivative in the duodenum of a patient, and second delayed release particles that are capable of releasing larazotide or derivative in the jejunum of a patient, and optionally a third delayed release particle capable of releasing larazotide or derivative in the ileum of a patient. Each particle may have a core particle, a coat comprising larazotide or derivative over the core particle, and a delayed-release coating (e.g., a 1:1 co-polymer of acrylate and methacrylate) outside the coat comprising larazotide or derivative. Whereas the first delayed-release particles release at least 70% of the larazotide or derivative in the first delayed-release particles by about 60 minutes of exposure to simulated intestinal fluid having a pH of greater than 5; the second delayed-release particles release at least 70% of the larazotide or derivative by about 30 and about 90 minutes of exposure to simulated intestinal fluid having a pH of greater than 5. The third delayed-release particles release at least 70% of the larazotide or derivative by about 120 minutes to about 240 minutes (e.g., about 120 minutes to about 180 minutes) of exposure to simulated intestinal fluid.

In some embodiments where the damage to the colon is involved, the larazotide or derivative may be administered to the colon of a patient, as an oral dosage, modified-release composition. Various colon-specific delivery approaches may be utilized. For example, the modified release formulation may be formulated using a colon-specific drug delivery system (CODES) as described for example, in Li et al., AAPS PharmSciTech (2002), 3(4): 1-9, the entire contents of which are incorporated herein by reference. Drug release in such a system is triggered by colonic microflora coupled with pH-sensitive polymer coatings. For example, the formulation may be designed as a core tablet with three layers of polymer. The first coating is an acid-soluble polymer (e.g., EUDRAGIT E), the outer coating is enteric, along with a hydroxypropyl methylcellulose barrier layer interposed in between. In another embodiment, colon delivery may be achieved by formulating the larazotide or derivative with specific polymers that degrade in the colon such as, for example, pectin. The pectin may be further gelled or cross-linked with a cation such as a zinc cation. Additional colon specific formulations include, but are not limited to, pressure-controlled drug delivery systems (prepared with, for example, ethylcellulose) and osmotic controlled drug delivery systems (i.e., ORDS-CT).

In various embodiments, the compositions of the present invention may use one or more modified-release coatings such as delayed-release coatings to provide for effective, delayed yet substantial delivery of the larazotide or derivative to the GI tract. For example, a composition can be enteric coated to delay release of the larazotide or derivative until it reaches the small intestine or the large intestine.

In an embodiment, the composition may remain essentially intact, or may be essentially insoluble, in gastric fluid. In some embodiments, the stability of the delayed-release coating can be pH dependent. Delayed-release coatings that are pH dependent will be substantially stable in acidic environments (pH of about 5 or less), and substantially unstable in near neutral to alkaline environments (pH greater than about 5). For example, the delayed-release coating may essentially disintegrate or dissolve in near neutral to alkaline environments such as are found in the small intestine (e.g. one or more of the duodenum, jejunum, and ileum) and/or large intestine (e.g. one or more of the cecum, ascending colon, transverse colon, descending colon, and sigmoid colon).

In some embodiments, the delayed-release coating (including for sustained release and controlled release formulations) includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT-type polymer (poly(methacrylic acid, methylmethacrylate), hydroxypropyl methylcellulose acetate succinate, cellulose acetate trimellitate, shellac or other suitable enteric coating polymers. The EUDRAGIT®-type polymer include, for example, EUDRAGIT® FS 30D, L 30 D-55, L 100-55, L 100, L 12.5, L 12.5 P, RL 30 D, RL PO, RL 100, RL 12.5, RS 30 D, RS PO, RS 100, RS 12.5, NE 30 D, NE 40 D, NM 30 D, S 100, S 12.5, and S 12.5 P. In some embodiments, one or more of EUDRAGIT® FS 30D, L 30 D-55, L 100-55, L 100, L 12.5, L 12.5 P RL 30 D, RL PO, RL 100, RL 12.5, RS 30 D, RS PO, RS 100, RS 12.5, NE 30 D, NE 40 D, NM 30 D, S 100, S 12.5 and S 12.5 P is used. The enteric agent may be a combination of the foregoing solutions or dispersions.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, EUDRAGIT NE®, polyvinyl esters, polyvinyl acetals, polyacrylic acid esters, butadiene styrene copolymers, and the like.

In some embodiments, the stability of the pharmaceutical composition can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine. In certain embodiments, the stability of the composition can be dependent on the presence of a microbial enzyme present in the gut flora. Accordingly, in various embodiments, the delayed-release coating is degraded by a microbial enzyme present in the gut flora. In an embodiment, the delayed-release coating is degraded by a bacteria present in the small intestine. In another embodiment, the delayed-release coating is degraded by a bacteria present in the large intestine.

The present invention also provides for compositions that release multiple doses of the larazotide or derivative along the gastrointestinal tract. For example, the composition and/or formulation can release multiple doses of the larazotide or derivative at different locations along the intestines, at different times, and/or at different pH. The overall release profile of such a formulation may be adjusted using, for example, multiple particle types or multiple layers. For example, in one embodiment, a first dose of the larazotide or derivative may be formulated for release in, for example, the small intestine (e.g., one or more of duodenum, jejunum, ileum), whereas a second dose is formulated for delayed release in, for example, the large intestines (e.g., one or more of cecum, ascending, transverse, descending or sigmoid portions of the colon, and rectum). In various embodiments, the composition and/or formulation may release at least three doses, at least four doses, or at least five doses of the larazotide or derivative at different locations along the intestines, at different times, and/or at different pH.

Larazotide or derivative can be administered in unit dosage forms (e.g., tablets, capsules, or solutions). For example, larazotide or derivative (or salt thereof) can be administered at from about 0.1 mg to about 5 mg, or at from about 0.1 mg to about 2 mg, or at from about 0.25 mg to about 1 mg, or at from about 0.5 mg to about 1 mg, or at from about 0.25 to about 0.75 mg. In various embodiments, the unit dose contains at least 1 mg of larazotide or derivative, or contains at least 1.5 mg or at least 2 mg of larazotide or derivative.

In accordance with certain embodiments of the invention, larazotide or derivative is administered more than once daily to promote GI tight junction integrity. For example, larazotide or derivative may be administered about two times daily, about three times daily, about four times daily, or about five times daily.

In various embodiments, the regimen of larazotide or derivative is administered for a prolonged period. For example, the regimen of larazotide or derivative may be administered for at least about 1 week, at least about 2 weeks, at least about 3 weeks, at least about 4 weeks, at least about 8 weeks, at least about 10 weeks, or at least about 12 weeks. In some embodiments, the regimen of larazotide or derivative is administered for at least about 1 month, at least about 2 months, at least about 4 months, and at least about 8 months. For example, the regimen of larazotide or derivative is administered for at least about 6 months.

In some embodiments, the patient may receive adjunct therapy, which in some embodiments is synergistic with larazotide treatment, including ameliorating dysbiosis and/or small intestinal bacterial overgrowth. In some embodiments, an antibiotic therapy is administered, followed by probiotic therapy to manage dysbiosis.

In some embodiments, the additional therapeutic agent is an antibacterial agent such as an antibiotic. Antibiotics suitable for use in the present invention include, but are not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norfliox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem).

In some embodiments, the subject receives an antiviral agent, including for patients having viral hepatitis. Exemplary antiviral agents include, but are not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet.

In some embodiments, the subject receives a probiotic, optionally following antibiotic therapy. Probiotics suitable for use in the present invention include, but are not limited to, *Saccharomyces boulardii*; *Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei*, *Lactobacillus acidophilus* (Bio-K+CL1285); combination of *Lactobacillus casei*, *Lactobacillus bulgaricus*, *Streptococcus thermophilus* (Actimel); combination of *Lactobacillus acidophilus*, *Bifidobacterium bifidum* (Florajen3); combination of *Lactobacillus acidophilus*, *Lactobacillus bulgaricus delbrueckii* subsp. *bulgaricus*, *Lactobacillus bulgaricus casei*, *Lactobacillus bulgaricus plantarum*, *Bifidobacterium longum*, *Bifidobacterium infantis*, *Bifidobacterium breve*, and *Streptococcus salivarius* subsp. *thermophilus* (VSL#3)).

EXAMPLES

Intestinal epithelial tight junction integrity is crucial to maintain an intact intestinal barrier against noxious luminal contents. Larazotide facilitates assembly of interepithelial tight junctions. Porcine mucosa injured by ischemia/reperfusion injury is abnormally permeable until interepithelial tight junctions have re-assembled.

We evaluated whether larazotide would enhance recovery of barrier function in ischemic-injured porcine jejunum. Yorkshire-cross pigs 6-8-weeks-of-age were anesthetized, followed by midline laparotomy and creation of a series of 10 cm intestinal loops commencing proximal to the ileum by ligating the intestinal lumen. The local mesenteric vasculature was ligated to select treatment loops for 45-min, whereas other loops were left as non-ischemic controls. Loops were subsequently resected, and the mucosal tissues were stripped in oxygenated (95% $O_2$/5% $CO_2$) Ringers from the muscle layers in preparation for ex vivo incubation in Ussing chambers. Tissues were monitored by measuring transepithelial resistance (TER) for 240-min. At the end of a 240-min recovery period, tissues were taken for histology and immunofluorescence evaluation of tight junction proteins.

Figure 2:
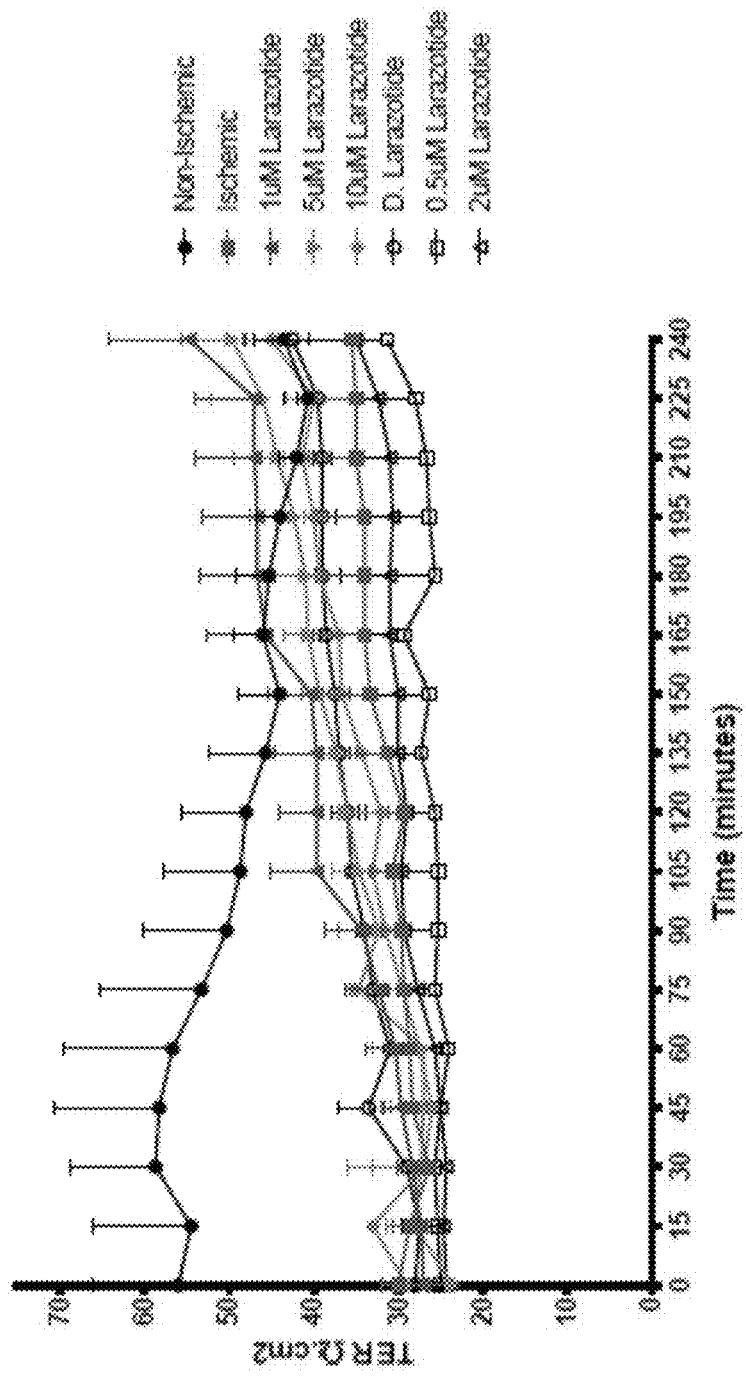
FIG. 2 is an additional dose response study showing that ischemic-injured tissues treated with larazotide alone showed a dose-dependent and significant (P<0.05) increase in recovery of TER as compared to untreated ischemic tissues.

Ischemic-injured tissues treated with larazotide alone showed a dose-dependent and significant ($P<0.05$) increase in recovery of TER as compared to untreated ischemic tissues, with the optimal dose of 1-micromole of larazotide (FIGS. 1 and 2).

Figure 3:
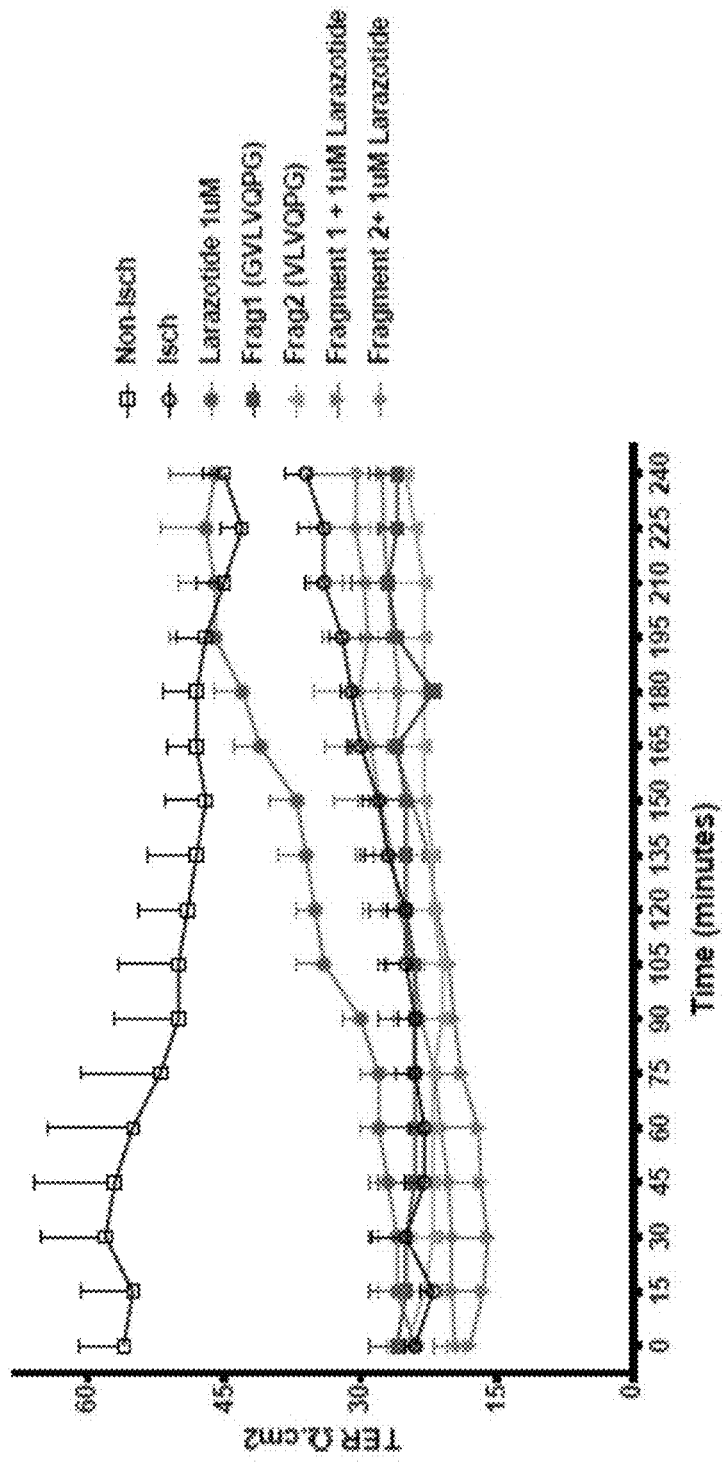
FIG. 3 and FIG. 4 show that the effect of larazotide was blocked with the fragments GVLVQPG (SEQ ID NO:2) and VLVQPG (SEQ ID NO:3).
Figure 4:
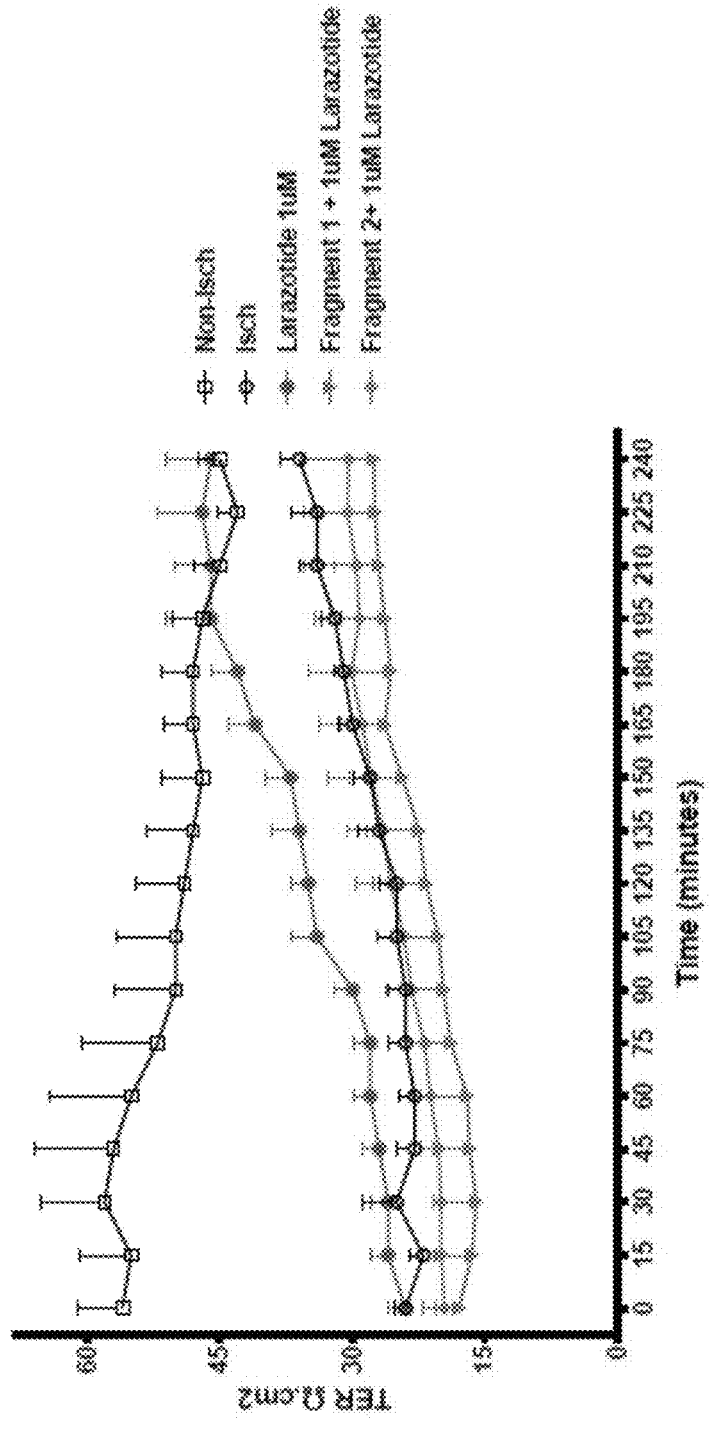

Larazotide consistently stimulates repair at 1 µM, but not at 0.1 or 10 µM. This effect may be due to generation of Larazotide fragments that act as competitive inhibitors. For example, the effect of Larazotide was blocked with the fragments GVLVQPG (SEQ ID NO:2) and VLVQPG (SEQ ID NO:3) (FIGS. 3 and 4). These fragments are presumed to be the first that would appear in the intestinal lumen in the presence of the amino peptidases.

Figure 5:
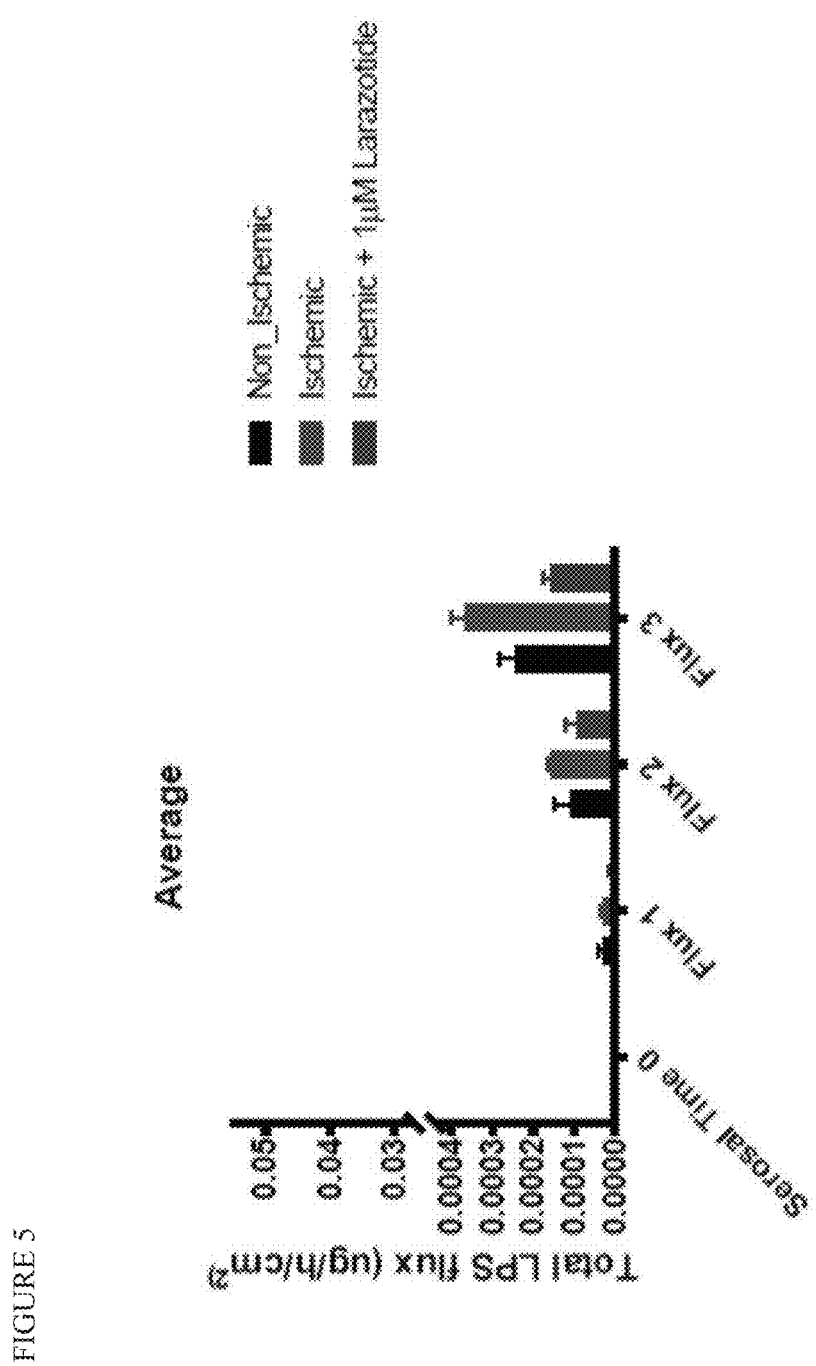
FIG. 5 shows that the larazotide-induced recovery of barrier function is also associated with reductions in lipopolysaccharide permeability across recovering tissue.
Figure 6:
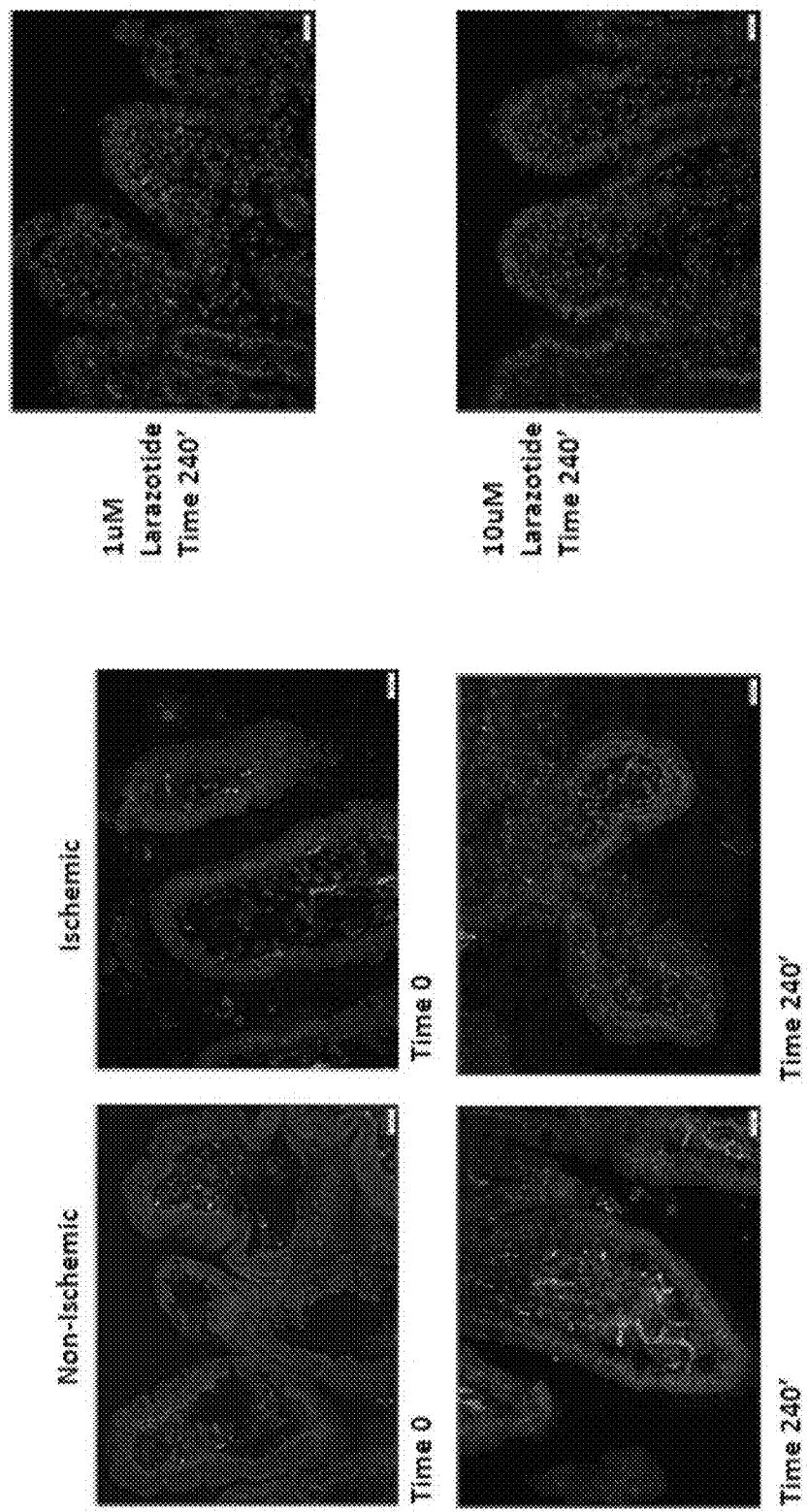
FIG. 6 shows increased localization of the tight junction sealing protein occludin in tissues treated with larazotide.
Figure 7A:
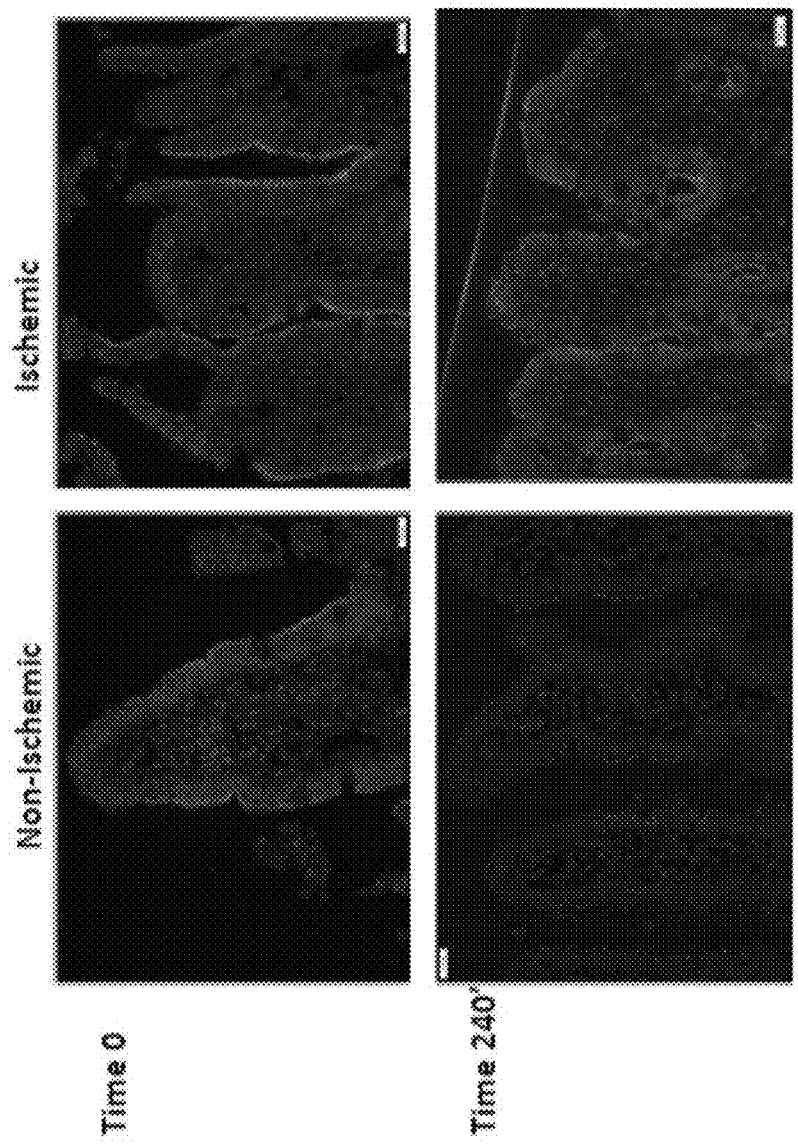
FIG. 7A shows pore (leak)-forming tight junction protein claudin 2 in ischemic and non-ischemic tissues.
Figure 7B:
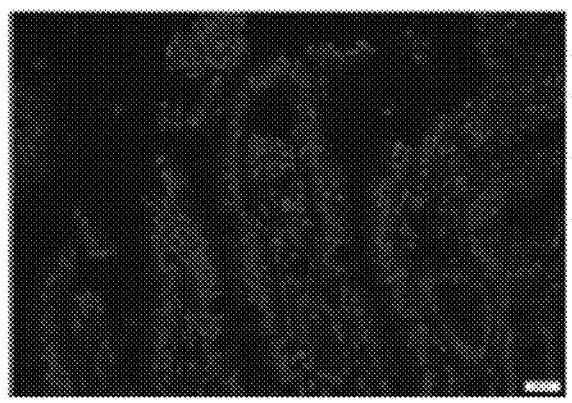
FIG. 7B shows pore (leak)-forming tight junction protein claudin 2 in tissues treated with larazotide.
Figure 7B:
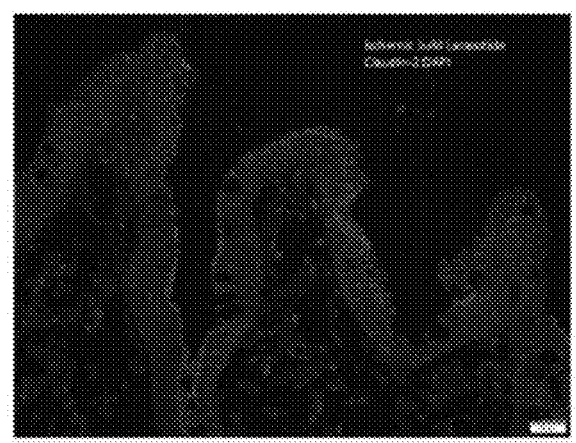
Figure 7B:
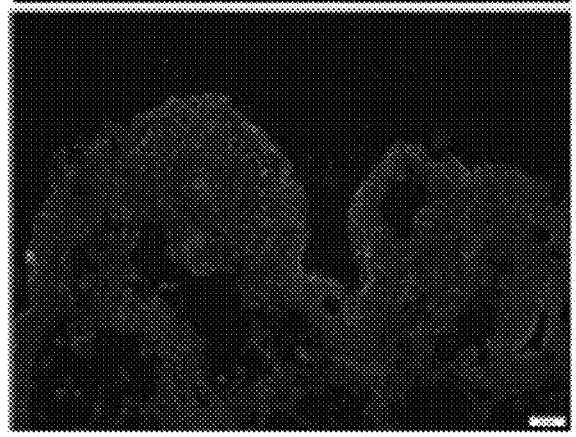

The larazotide-induced recovery of barrier function is also associated with reductions in lipopolysaccharide permeability across recovering tissue (FIG. 5), which is likely to be beneficial in patients with diseases associated with LPS-induced conditions such as NASH and sepsis. The mechanism of larazotide on leaky intestinal mucosa appears to be related to a specific action on tight junctions, based on increased localization of the tight junction sealing protein occludin (FIG. 6) and reductions in the pore (leak)-forming tight junction protein claudin 2 (FIGS. 7A,B).

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The invention claimed is:

1. A method for treating a subject having an ischemic intestinal condition selected from ischemic colitis and intestinal volvulus, comprising administering an effective amount of larazotide, or a larazotide derivative having one or two amino acid modifications with respect to SEQ ID NO: 1 and/or having one or more (d)-amino acids, to the subject, wherein the larazotide or derivative is administered in a sustained release or controlled release formulation that releases from about 0.5 to about 5 mg of larazotide or derivative to the small and/or large intestine, and wherein the formulation releases peptide for at least about 2 hours during exposure to simulated intestinal fluid.

2. The method of claim 1, wherein the ischemic colitis is mild to moderate.

3. The method of claim 1, wherein the ischemic colitis is severe.

4. The method of claim 1, wherein the larazotide is larazotide acetate.

5. The method of claim 1, wherein the sustained release or controlled release formulation releases larazotide or derivative over at least 210 minutes in simulated intestinal fluid.

6. The method of claim 1, wherein the composition comprising larazotide or derivative releases larazotide or derivative in the small intestine.

7. The method of claim 6, wherein the larazotide or derivative is released in one or more of the duodenum, jejunum and ileum.

8. The method of claim 6, wherein different compositions target release of Larazotide or derivative in the small intestine and large intestine.

9. The method of claim 1, wherein the composition comprising larazotide or derivative is administered more than once daily.

10. The method of claim 1, further comprising, administering antibiotic therapy.

11. The method of claim 1, further comprising, administering antiviral therapy.

12. The method of claim 1, further comprising administering a probiotic.

13. The method of claim 1, wherein the sustained release or controlled release formulation targets delivery of the larazotide or derivative to the jejunum and ileum.

14. The method of claim 1, wherein the sustained release or controlled release formulation comprises a biodegradable matrix.

15. The method of claim 14, wherein the sustained release or controlled release formulation has a gastric resistant coating that begins to release the larazotide or derivative within about 5 to about 30 minutes of exposure to simulated intestinal fluid.

16. The method of claim 15, wherein the release of the larazotide or derivative continues for at least about 180 minutes, in simulated intestinal fluid.

17. The method of claim 1, wherein the sustained release or controlled release formulation comprises an enteric coating selected from methacrylic acid copolymers, cellulose acetate phthalate, hydroxypropylmethyl cellulose phthalate, polyvinyl acetate phthalate, carboxymethylethykellulose, poly(methacrylic acid, methylmethacrylate, hydroxypropyl methylcellulose acetate, succinate, cellulose acetate trimellitate, and shellac.

18. The method of claim 15, wherein the release of the larazotide or derivative continues for at least about 210 minutes in simulated intestinal fluid.

19. The method of claim 15, wherein the release of the larazotide or derivative continues for at least about 240 minutes in simulated intestinal fluid.

20. The method of claim 15, wherein the release of the larazotide or derivative continues for at least about 280 minutes in simulated intestinal fluid.

21. The method of claim 6, wherein the larazotide or derivative is released in one or more of the colon transversum, colon descendens, colon ascendens, colon sigmoidenum, and cecum.

22. A method for treating a subject having an ischemic intestinal condition selected from ischemic colitis and intestinal volvulus, comprising administering an effective amount of larazotide, or a larazotide derivative having one or two amino acid modifications with respect to SEQ ID NO: 1 and/or having one or more (d)-amino acids, to the subject.

23. The method of claim 22, wherein the ischemic colitis is mild to moderate.

24. The method of claim 22, wherein the ischemic colitis is severe.

* * * * *

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide.

<400> SEQUENCE: 1

Gly Gly Val Leu Val Gln Pro Gly
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide.
```

```
<400> SEQUENCE: 2

Gly Val Leu Val Gln Pro Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide.

<400> SEQUENCE: 3

Val Leu Val Gln Pro Gly
1               5
```